United States Patent [19]
Frohning et al.

[11] Patent Number: 6,096,931
[45] Date of Patent: Aug. 1, 2000

[54] PROCESS FOR PREPARING ALCOHOLS

[75] Inventors: Carl Dieter Frohning, Wesel; Wolfgang Zgorzelski, Oberhausen; Hans Liebern, Mulheim an der Ruhr, all of Germany

[73] Assignee: Celanese GmbH, Germany

[21] Appl. No.: 09/204,597

[22] Filed: Dec. 3, 1998

[30] Foreign Application Priority Data

Dec. 10, 1997 [DE] Germany .......................... 197 54 848

[51] Int. Cl.⁷ .................................................. C07C 29/14
[52] U.S. Cl. ........................ 568/881; 568/880; 568/862
[58] Field of Search ................................... 568/881, 862, 568/880

[56] References Cited

FOREIGN PATENT DOCUMENTS

| | | |
|---|---|---|
| 690249 | 5/1967 | Belgium . |
| 0421196 | 4/1991 | European Pat. Off. . |
| 0537605 | 4/1993 | European Pat. Off. . |
| 1643856 | 11/1971 | Germany . |
| 4134497 | 4/1993 | Germany . |

OTHER PUBLICATIONS

Tsunekazu et al, "Method . . . Higher Aldehyde", Patents Abstracts of Japan, vol. 1, No. 383, p 4, Abstract No. JP 61172838 (1998) Abstract Only.

"Hydrogenation . . . Aliphatic Tert Amine", 1998 Derwent Information Ltd., JP61172838A Abstract Only.

*Primary Examiner*—Paul J. Killos
*Attorney, Agent, or Firm*—Bierman, Muserlian and Lucas

[57] ABSTRACT

In a process for preparing alcohols comprising the hydrogenation of aldehydes in the presence of a hydrogenation catalyst in the gas phase, the improvement comprising adding nitrogen-containing bases to the aldehyde to be hydrogenated, whereby the formation of by-products is largely suppressed and isolation of the desired alcohols in high selectivity and correspondingly high yield is made possible.

13 Claims, No Drawings

PROCESS FOR PREPARING ALCOHOLS

The invention relates to a process for preparing alcohols by hydrogenation of aldehydes in the gaseous phase.

STATE OF THE ART

It is known that alcohols can be prepared by catalytic hydrogenation of the corresponding saturated and unsaturated aldehydes at elevated temperature and at atmospheric or superatmospheric pressure. The reaction can be carried out either batchwise or continuously in a homogeneous or heterogeneous phase. Correspondingly, the hydrogenation catalyst is used either in dissolved form or in finely divided form as a suspension or in granule or pellet form as a fixed-bed catalyst. The compounds to be hydrogenated can be supplied to the catalyst in a gaseous or liquid state.

Particularly, the hydrogenation of saturated aldehydes which are obtained by hydroformylation of alkenes and the hydrogenation of $\alpha,\beta$-unsaturated aldehydes which are formed by aldolization of aldehydes are of great importance. Among these, the hydrogenation of n- and iso-butyraldehyde, n- and iso-valeraldehyde, hydroxy-pivalaldehyde, n- and iso-hexanal, 2-ethylhexenal, mixtures of isomeric nonenals and/or isomeric nonanals and also mixtures of isomeric decenals and/or isomeric decanals are of particular industrial relevance.

A comprehensive discussion of the preparation of alcohols by catalytic hydrogenation of carbonyl compounds, in particular ketones, aldehydes and their derivatives, may be found in Houben-Weyl, Methoden der organischen Chemie, Georg Thieme Verlag, Stuttgart-New York 1984, volume VI/lb, pages 9 to 111.

In hydrogenations in the liquid phase, reactor pressures of from 20 to 300 bar are customary to achieve satisfactory hydrogenation. Furthermore, the hydrogenation frequently has to be carried out in a plurality of stages (DE-B-12 31 227). Since the reaction is strongly exothermic, recirculation of a considerable part of the hydrogenated product or dilution with a solvent for capacitive heat removal is necessary in industrial reactors. This permits only comparatively low aldehyde space velocities through the reactors, as a result of which the formation of undesired downstream products of the reactive aldehydes is promoted because of the consequently high residence time. These difficulties can be avoided by hydrogenation in the gas phase.

The hydrogenation of readily vaporizable aldehydes is therefore preferably carried out in the gas phase at elevated pressures and temperatures in the presence of various, predominantly nickel- and/or copper-containing catalysts.

Thus, EP-A-0 421 196 discloses a process for preparing alcohols in which organic carbonyl compounds are reacted with hydrogen in the gas phase at a temperature of from 60 to 150° C. and at atmospheric or superatmospheric pressure in the presence of a supported catalyst comprising nickel, aluminum oxide and zirconium dioxide.

However, the hydrogenation of aldehydes in the gas phase over such nickel- and/or copper-containing catalysts likewise results in formation of by-products which reduce the yield of the desired alcohols albeit to a lesser extent than when working in the liquid phase. Numerous efforts in this field have therefore been directed at improving the selectivity of the hydrogenation reaction and thus the yield of desired products by further development of the catalysts to be used.

Thus, Belgian Patent 690 249 discloses a process for preparing saturated aliphatic alcohols by catalytic hydrogenation of aldehydes in the gas phase, in which a copper/nickel catalyst on a silica gel support is used in the 1st stage and a nickel- and/or palladium-containing catalyst is used in the 2nd stage. This process allows the preparation of saturated alcohols in sensible yields under mild conditions. However, a disadvantage is the great sensitivity of the supported catalysts comprising silica gel, for example to unforeseen malfunctions such as temperature increases or to impurities which can easily lead to permanent damage to the catalyst. In particular, these catalysts are not suitable for regeneration by burning off the impurities at high temperatures, since the formation of by-products such as hydrocarbons and ethers is generally considerably increased when the catalysts which have been regenerated by such a high-temperature treatment are reused in a hydrogenation reaction.

The importance of the pH of the surface of the hydrogenation catalysts for the formation of undesired by-products was recognized long ago. Thus, Journal of Catalysis, Vol. 128, pp. 337–351 (1991) describes the formation of ether by-products in aldehyde hydrogenation in the presence of acid centers on the surface of $Ni/SiO_2$ catalysts. To reduce ether formation, DE-C 16 43 856 describes hydrogenation over copper- and/or nickel-containing supported catalysts comprising silica gel in which the pH of the silica gel surface is set at 6–10. However, in the case of a high space velocity over the catalyst, formation of saturated and unsaturated hydrocarbons occurs to an increasing extent for these catalysts too, thereby reducing the selectivity of the hydrogenation and also the yield of desired product.

The unsaturated hydrocarbons are formed by decarbonylation, i.e. by elimination of the carbonyl group from the aldehydes used, and thus have one carbon atom less than the aldehyde used. Subsequent hydrogenation then leads to formation of the saturated hydrocarbons and of methane from carbon monoxide. The hydrogenation of carbon monoxide to methane is strongly exothermic, which leads to an increased temperature in the catalyst bed and as a result again to increased formation of undesired by-products.

EP-A 0 470 344 discloses a two-stage hydrogenation of aldehydes, in which a specific copper catalyst which has been made alkaline is used in the 1st stage and a specific nickel catalyst is used in the 2nd stage and over 85% of the hydrogenation reaction is carried out in the 1st stage. Here too, the formation of hydrocarbons having one carbon atom less than the desired alcohol and of ethers and esters having twice the number of carbon atoms as the aldehyde used is observed. The esters are formed from the aldehyde used by a Tishtshenko reaction.

U.S. Pat. No. 4,626,604 describes an at least three-stage process using different catalysts for hydrogenating unsaturated compounds to avoid formation of the by-products mentioned. A disadvantage of this process is the extraordinary complexity which is caused by use of different conditions for the respective catalysts and their different operating time.

The formation of hydrocarbons, ethers, esters and acetals as by-products of the hydrogenation reaction not only reduces the yield, but also incurs considerable costs in the isolation of the pure alcohols where, in particular, the removal of the ethers presents particular difficulties because of their boiling point and can be achieved only at high expense.

To avoid formation of the by-products mentioned, not only have improved catalysts been made available and multistage reaction procedures been proposed in the past, but a series of further measures have also been developed. Thus, for example, dilution of the vapor stream entering the hydrogenation, which comprises an excess of hydrogen in addition to the aldehydes to be hydrogenated, has an advantageous effect. This makes it possible to reduce by-product formation by means of a high hydrogen excess or a low concentration of the aldehydes in the vapor stream.

A disadvantage of this measure is the low specific throughput of the aldehyde to be hydrogenated or the necessity of a high hydrogen excess which has to be circulated for economic reasons. Furthermore, it is known that the addition of water can lead to a reduction in by-product formation. The procedure here is that water vapor in a concentration of a few % by volume is added to the stream entering the hydrogenation. However, this water has to be completely removed again after the condensation of the product alcohols, which makes the process complicated.

OBJECTS OF THE INVENTION

It is an object of the invention to provide a process by which the formation of by-products in the hydrogenation of aldehydes over hydrogenation catalysts in the gas phase is largely suppressed and the isolation of the desired alcohols in high selectivity and correspondingly high yield is made possible simply and inexpensively.

This and other objects and advantages will become obvious from the following detailed description.

THE INVENTION

This object is achieved by a process for preparing alcohols by hydrogenation of aldehydes in the presence of a hydrogenation catalyst in the gas phase, wherein nitrogen-containing bases are added to the aldehyde to be hydrogenated.

The nitrogen-containing bases are usually primary, secondary or tertiary amines of formula I or diamines of formula II

 $NR_3$     I

 $R_2N—(CH_2)_x—NR_2$     II where the Rs are individually selected from the group consisting of hydrogen, alkyl of 2 to 10 carbon atoms, cycloalkyl of 5 to 10 carbon atoms, and hydroxyalkyl of 2 to 10 carbon atoms and x is an integer from 2 to 6. Preferred branched or unbranched alkyls are ethyl, propyl, n- or i-butyl, n- or i-pentyl, hexyl, heptyl and octyl radicals. As branched or unbranched hydroxyalkyls, preference is given to 2-hydroxyethyl, 2-hydroxypropyl and 3-hydroxypropyl.

As diamines of formula II, particular preference is given to using ethylenediamine, propylene-diamine or 1,4-diaminobutane, in which x is 2, 3 or 4 and all Rs are hydrogen.

However, other nitrogen-containing bases can also, in principle, be used in the process of the invention as long as they have a sufficiently high vapor pressure to be able to be added in vapor form to aldehydes in amounts of from 1 to 50 ppm, preferably 1 to 25 ppm, calculated in ppm of nitrogen based on the aldehyde used, under the hydrogenation condition selected. In the hydrogenation of 2-ethylhexenal to 2-ethylhexanol, for example, the addition of tri-i-octylamine in an amount of from 1 to 20 ppm of nitrogen, based on the aldehyde used, (corresponding to 25.2–504 ppm of tri-i-octylamine) has been found to be useful for significantly reducing the formation of hydrocarbons, ethers and esters.

Aldehydes which can be used are saturated or unsaturated aldehydes having 2 to 10 carbon atoms or mixtures of these. The aldehydes can be used in relatively pure form or else as crude reaction products as are obtained in the preparation by means of hydroformylation, aldol condensation, substitution or addition, possibly in dilute solutions.

Examples of saturated aldehydes are acetaldehyde, propanal, n- and i-butyraldehyde, n- and i-pentanal, n- and i-hexanal, n- and i-heptanal, n- and i-octanal, preferably 2-ethylhexanal, n- and i-nonanal, n- and i-decanal.

Examples of unsaturated aldehydes which can be used are acrolein, crotonaldehyde, n- and i-pentenal, n- and i-hexenal, hexadienal, n- and i-heptenal, n- and i-octenal, preferably 2-ethylhexenal, n- and i-nonenal and also n- and i-decenal.

However, it is also possible to use other aldehyde derivatives which can be prepared by a series of customary syntheses such as aldolization, aldol condensation, substitution or addition reactions, for example the addition of water onto unsaturated aldehydes, and can be successfully converted into the corresponding alcohols by the process of the invention. These aldehyde derivatives can be, for example, relatively high molecular weight aldehydes, ring-containing aldehydes, bifunctional aldehydes or aldehydes which contain further functional groups such as hydroxyl groups.

Preferably, the process of the invention is applied to the hydrogenation of the n- and i-butyraldehyde, n- and i-valeraldehyde and 2-ethylhexenal.

The hydrogenation of the aldehydes can be carried out in the presence of customary hydrogenation catalysts. Nickel- and/or copper-containing catalysts and also noble metal catalysts based on platinum, palladium, rhodium or ruthenium have been found to be particularly useful. For the complete hydrogenation of unsaturated aldehydes such as 2-ethylhexenal, it is possible to use the nickel- and/or palladium-containing catalysts known from G.B. 1,276,618. The catalysts can be applied to support materials such as $SiO_2$ and/or $Al_2O_3$ of various types. The copper catalysts supported on zinc oxide and known from U.S. Pat. No. 2,549,416 can also be used for the gas-phase hydrogenation of aldehydes.

Furthermore, the catalysts known for the hydrogenation of sulfur-containing starting materials from naphtha crackers can also be employed in the process of the invention. Suitable catalysts of this type are known from, for example, U.S. Pat. No. 2,709,714, U.S. Pat. No. 2,760,994, SU 179,757 and SU 638,585. As activators and promoters, the catalysts used can further comprise oxides of various monovalent to pentavalent metals. These are, for example, the oxides of Zn, Mg, Mn, Cr, Zr, Fe or of rare earth metals. Phosphates, tungstates, chromates, dichromates, molybdates, pyroacids and polyacids of sulfur, phosphorus, boron, molybdenum, titanium and tungsten or their salts can also be present. It is also possible to add silver, palladium or ruthenium to copper- and/or nickel-containing catalysts.

Further catalysts which are suitable for the process of the invention are described, for example, in Hydrocarbon Processing 1993, 67.

A specific catalyst which can be used successfully is that described in EP-A-0 421 196, which comprises 20–90% by weight of nickel, based on the catalyst composition, and 1–30, preferably 3–15 and most preferably 4–10, parts by weight of aluminum oxide and 0.5–20, preferably 1–10 and most preferably 1.5–5, parts by weight of zirconium dioxide, in each case based on 100 parts by weight of nickel, as coprecipitate on a support material.

Suitable support materials are activated carbon, aluminas, pumice, $\gamma$-$Al_2O_3$, $SiO_2$, silica gel, kieselguhr and siliceous earths. $siO_2$, silica gel, kieselguhr and siliceous earth have been found to be particularly useful. Use is usually made of 6–80, preferably 15–65 and in particular 35–50, parts by weight of support material per 100 parts by weight of nickel. The preparation of these catalysts is described in EP-A-0 421 196 which is hereby expressly incorporated by reference.

Also suitable are the copper oxide/zinc oxide/aluminum oxide catalysts claimed in EP-A-0 604 792, which comprise, per 100 parts by weight of copper oxide, 40–130 parts by weight of zinc oxide, 2–50 parts by weight of aluminum oxide and 1–4 parts by weight of sodium oxide, have a total BET surface area of 50–100 $m^2/g$ and in which 75–95% of the total surface area is made up by pores having radii of 9–1000 nm and 5–25% of the total surface area is made up by pores having radii of less than 9 nm. The description of 15 these catalysts in EP-A-0 604 792 is hereby expressly incorporated by reference.

It is also possible to use the catalysts claimed in EP-A-0 618 006 in the process of the present invention. These are hydrogenation catalysts comprising 25–50% by weight of metallic nickel, 10–35% by weight of nickel oxide, 4–12% by weight of magnesium oxide, 1–5% by weight of sodium oxide and the balance support material, where the sum of nickel and nickel oxide is 40–70% by weight, the total BET surface area is 80–200 $m^2/g$ and the total pore volume determined by mercury porosimetry is 0.35–0.6 ml/g, where 30–60% of the total pore volume is made up by pores having a radius of $\leq 40$Å, 4–10% of the total pore volume is made up by pores having a radius of from >40 to 300 Å and 30–60% of the total pore volume is made up by pores having a radius of from >300 to 5000 Å. The description of these catalysts in EP-A-0 618 006 is hereby expressly incorporated by reference.

Also suitable is the hydrogenation catalyst described in EP-A-0 528 305, which comprises, per 100 parts by weight of copper oxide, 40–130 parts by weight of zinc oxide, 2–50 parts by weight of aluminum oxide and, optionally, 0.5–8 parts by weight of manganese oxide, molybdenum oxide, vanadium oxide, zirconium oxide and/or alkaline earth metal oxide and has a total BET surface area of 80–175 $m^2/g$ of catalyst in the unreduced state, where 75–95% of the total BET surface area is made up by pores having a radius $r_p \leq 15$ nm. The description of these catalysts in EP-A-0 528 305 is hereby expressly incorporated by reference.

To carry out the hydrogenation, the aldehyde and the nitrogen-containing base are vaporized together and passed in admixture with hydrogen over the granular/pelletized catalyst arranged as a fixed bed in a reaction vessel. Use is made of at least 2 moles, preferably 2–100 moles and more preferably 3–30 moles, of hydrogen per equivalent of the aldehyde to be hydrogenated. Unreacted hydrogen can be recirculated to the reaction.

The vapors leaving the reaction vessel are condensed and the condensate is, if necessary, worked up by distillation under atmospheric or reduced pressure. The hydrogenation temperature is generally 50–250° C., preferably 80–160° C. The choice of hydrogenation temperature is influenced by the boiling point of the aldehyde, the pressure and the amount of hydrogen used. The pressure is 0.01–2.5 MPa and can be selected freely within this range, taking account of the boiling point and the amount of hydrogen used so as to meet the requirement that the starting materials to be hydrogenated and the corresponding hydrogenated products remain in gaseous form. The process of the invention can be carried out continuously or batchwise.

When the process is carried out continuously, the space velocity, expressed as volume of liquid starting material/volume of catalyst x hour (V/Vh), is from 0.2 to 1.5, preferably from 0.3 to 1.2 and more preferably from 0.5 to 1.0.

Surprisingly, even very low concentrations of the nitrogen-containing bases of a few ppm, calculated as ppm of nitrogen based on the aldehyde used, are sufficiently effective to reduce the formation of the various by-products in the hydrogenation reaction substantially. Another considerable advantage is that the presence of the nitrogen-containing bases in low concentration in the aldehydes used for the hydrogenation does not lead to the known secondary reactions such as the Cannizzaro reaction or Claisen-Tishtshenko reaction. Thus, the overall selectivity of the hydrogenation of aldehydes is increased.

In the following examples, there are described several preferred embodiments to illustrate the invention. However, it should be understood that the invention is not intended to be limited to the specific embodiments.

The following general experimental description applies to all the examples:

An electrically heated jacket reactor (length: 1500 mm, internal diameter: 20 mm) was charged with 150 ml (140 g) of a commercial nickel catalyst (60% by weight of Ni, 27% by weight of kieselguhr, 3% by weight of $Al_2O_3$, 2% by weight of $ZrO_2$). After activating the catalyst, 90 g/h of n-butanal (purity 98.7%) were pumped in at a reactor jacket temperature of 105° C. and a pressure of 0.35 MPa (abs.). The n-butanal was vaporized in a vaporizer installed upstream of the reactor and was passed over the catalyst in vapor form. Together with the n-butanal, hydrogen (99% by volume of $H_2$; 1% by volume of $N_2$) was fed into the vaporizer in such an amount that the flow of gas leaving the vaporizer was 200 standard 1/h. The reaction products were cooled to 18° C. under the reaction pressure and were separated in a separator into a liquid and a gaseous product stream. The amounts of both product streams were measured and the streams were analyzed by gas chromatography. For the calculation of product losses by dissociation, it was assumed that 1 mole of methane was formed per mole of dissociated n-butanal.

COMPARATIVE EXAMPLE 1

To decrease the initial activity of the catalyst, the reaction was carried out under constant conditions over a period of 180 hours. After this time, the following data were determined (liquid product, % by weight):

| | |
|---|---|
| n-butanal | 0.04 |
| n-butanol | 84.91 |
| di-n-butyl ether | 14.61 |
| n-butyl n-butyrate | 0.14 |
| hydrocarbons | 0.30 | losses (dissociation, by-products): 15.2% by weight, based on n-butanal used)

COMPARATIVE EXAMPLE 2

To reduce by-product formation, 9 g/h of water (10% by weight, based on n-butanal) were fed into the vaporizer in addition to the n-butanal (90 g/h) and passed together with the vaporized n-butanal and hydrogen over-the catalyst. After a period of 266 hours of operation under these conditions, the following data were determined (liquid product, % by weight):

|  |  |
|---|---|
| n-butanal | 0.10 |
| n-butanol | 97.31 |
| di-n-butyl ether | 2.31 |
| n-butyl n-butyrate | 0.14 |
| hydrocarbons | 0.15 | losses (dissociation, by-products): 2.85% by weight, based on n-butanal used)

The addition of water reduced the losses, but the selectivity of the hydrogenation continues to be unsatisfactory.

EXAMPLE 1

90 g/h of n-butanal were fed into the reactor. Tri-iso octylamine was added to the n-butanal in an amount of 250 ppm (0.025% by weight based on n-butanal, corresponding to 9.9 ppm of nitrogen based on-n-butanal used). After an operating time of 158 hours, the following data were determined (liquid product, % by weight):

|  |  |
|---|---|
| n-butanal | 0.13 |
| n-butanol | 99.31 |
| di-n-butyl ether | 0.011 |
| n-butyl n-butyrate | 0.02 |
| hydrocarbons | 0.53 | losses (dissociation, by-products): 0.61% by weight, based on n-butanal used)

Various modifications of the process may be made without departing from the spirit or scope thereof and it is to be understood that the invention is intended to be limited only as defined in the appended claims.

What we claim is:

1. In a process for preparings alcohols by hydrogenation of aldehydes in the presence of a hydrogenation catalyst in the gas phase, the improvement comprises adding nitrogen-containing bases to the aldehyde to be hydrogenated in vapor form to the aldehyde in amounts of from 1 to 50 ppm, calculated in pm of nitrogen based on the aldehyde used.

2. The process of claim 1, wherein the nitrogen-containing bases are selected from the group consisting of primary, secondary or tertiary amines of formula I and diamines formula II

NR$_3$     I

R$_2$N—(CH$_2$)$_x$—NR$_2$     II wherein the Rs are individually selected from the group consisting of hydrogen, alkyl of 2 to 10 carbon atoms, cycloalkyl of 5 to 10 carbon atoms and hydroxyalkyl of 2 to 10 carbon atoms and x is an integer from 2 to 6.

3. The process of claim 2 wherein alkyl is selected from the group consisting of ethyl, propyl, n- and i-butyl, n- and i-pentyl, hexyl, heptyl and octyl, hydroxyalkyl is selected from the group consisting of 2-hydroxyethyl, 2-hydroxypropyl and 3-hydroxypropyl and in diamines of formula II, x is 2, 3 or 4 and all Rs are hydrogen.

4. The process of claim 1 wherein the aldehydes used are saturated or unsaturated aldehydes of 2 to 10 carbon atoms or mixtures thereof.

5. The process of claim 4 wherein the aldehydes are selected from the group consisting of acetaldehyde, propanal, n- and i-butyraldehyde, n- and i-pentanal, n- and i-hexanal, n- and i-heptanal, n- and i-nonanal, n- and i-decanal, acrolein, crotonaldehyde, n- and i-pentenal, n- and i-hexenal, hexadienal, n- and i-heptenal, n- and i-octenal, 2-ethylhexenal, n- and i-nonenal and n- and i-decenal.

6. The process of claim 1 wherein the hydrogenation of the aldehydes is carried out in the presence of a nickel- and/or copper-containing catalyst or a noble metal catalyst based on platinum, palladium, rhodium, or ruthenium, which catalyst is applied to a support material.

7. The process of claim 6 wherein the catalyst comprises 20 to 90% by weight of nickel, based on the catalyst composition, and 1 to 30 parts by weight of aluminum oxide and 0.5 to 20 parts by weight of zirconium dioxide, in each case based on 100 parts by weight of nickel, as coprecipitate on a support material.

8. The process of claim 1 wherein the aldehyde and the nitrogen-containing base are vaporized together and then are passed in admixture with hydrogen over the granular/pelletized catalyst arranged as a fixed bed in a reaction vessel, where at least 2 moles of hydrogen are used per equivalent of the aldehyde to be hydrogenated, the hydrogenation temperature is 50 to 250° C., and the pressure is 0.01 to 2.5 MPa.

9. The process of claim 1 carried out continuously at a space velocity, expressed as volume of liquid starting material/volume of catalyst x hour (V/Vh), of from 0.2 to 1.5.

10. The process of claim 1 wherein the nitrogen-containing base is added in an amount of 1 to 25 ppm.

11. The process of claim 7 wherein the catalyst comprises 4 to 10 parts by weight of aluminum oxide and 1.5 to 5 parts by weight of zirconium oxide.

12. The process of claim 8 wherein 2 to 100 moles of hydrogen are used and the hydrogenation temperature is 80 to 160° C.

13. The process of claim 9 wherein the space velocity is 0.5 to 1.0.

* * * * *